United States Patent
Nonaka et al.

(10) Patent No.: US 7,288,245 B2
(45) Date of Patent: Oct. 30, 2007

(54) COMPOSITION HAVING IMMUNOREGULATING ACTIVITIES

(75) Inventors: Yuji Nonaka, Ibaraki (JP); Takayuki Izumo, Osaka (JP); Keiko Iida, Kobe (JP)

(73) Assignee: Suntory Limited, Osaka (JP)

( * ) Notice: Subject to any disclaimer, the term of this patent is extended or adjusted under 35 U.S.C. 154(b) by 0 days.

(21) Appl. No.: 11/094,575

(22) Filed: Mar. 31, 2005

(65) Prior Publication Data

US 2005/0265984 A1 Dec. 1, 2005

(30) Foreign Application Priority Data

May 28, 2004 (JP) ............................ 2004-159461

(51) Int. Cl.
  A22C 13/00 (2006.01)
  A61K 45/00 (2006.01)
  A01N 63/00 (2006.01)

(52) U.S. Cl. .................. 424/93.45; 426/390; 426/531; 435/853

(58) Field of Classification Search .................... None
See application file for complete search history.

(56) References Cited

U.S. PATENT DOCUMENTS 7,063,836 B2 * 6/2006 Garner et al. ............ 424/93.45

FOREIGN PATENT DOCUMENTS

JP  10-167972  6/1998

OTHER PUBLICATIONS

A. Kishi et al., "Screening of Immune-enhancing Probiotics: Study of the immune-enhancing effects of *Lactobacilli* strains by in vitro simulation of human peripheral blood mononuclear cells," *Pasken Journal*, 2002, vol. 15, pp. 21-26 (Partial Translation provided).

K. Akatani et al., "Relationship among the presence of extracellular-polysaccharides, adherent pr9operties and immunomodulatory function of *Lactobacillus pentosus* strains isolated from pickles," 6th Japan Bifidus Foundation, *Journal of Intestinal Microbiology*, 2002, vol. 16, p. 15 (Partial Translation provided).

* cited by examiner

Primary Examiner—David M. Naff
Assistant Examiner—Deborah K. Ware
(74) Attorney, Agent, or Firm—Drinker Biddle & Reath LLP

(57) ABSTRACT

The invention provides a composition comprising novel lactic acid bacteria having immunoregulating activities. Specifically, the invention provides food, drinks or medicaments containing novel lactic acid bacteria separated from "Shibazuke," one kind of traditional Kyoto pickles, and having immunoregulating activities. The lactic acid bacteria belong to *Lactobacillus pentosus* and have a weak assimilating activity or no assimilating activity for glycerol.

7 Claims, 12 Drawing Sheets

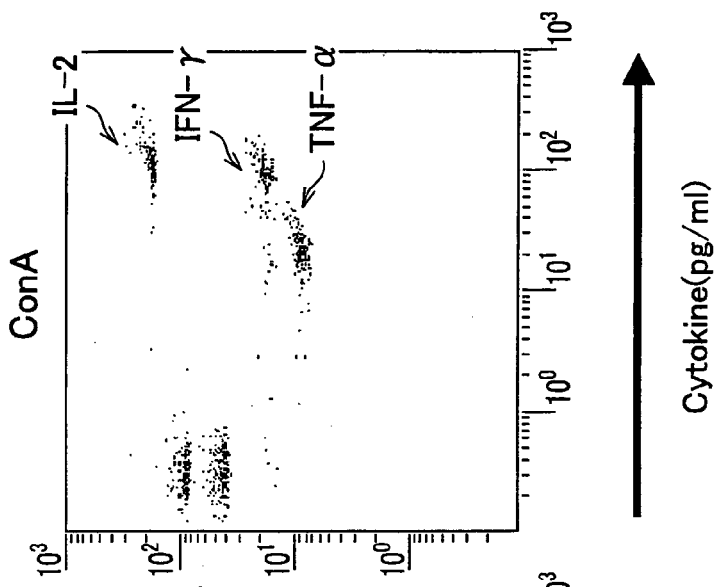
FIG. 4(c) ConA
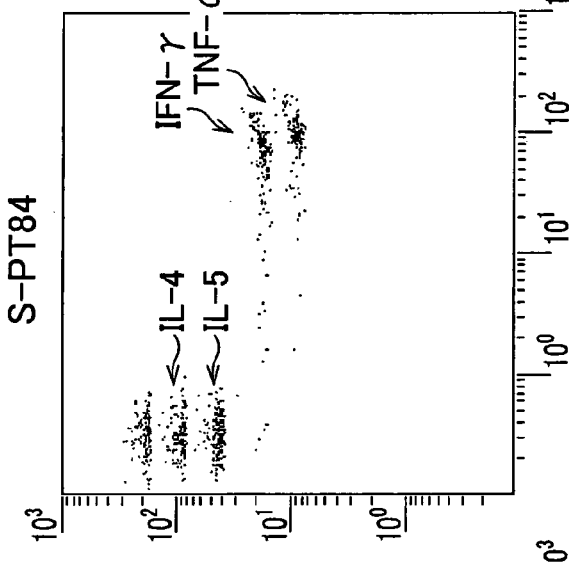
FIG. 4(b) S-PT84
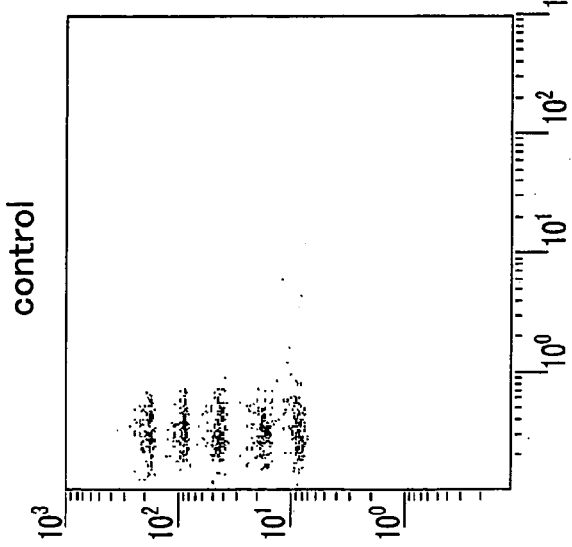
FIG. 4(a) control

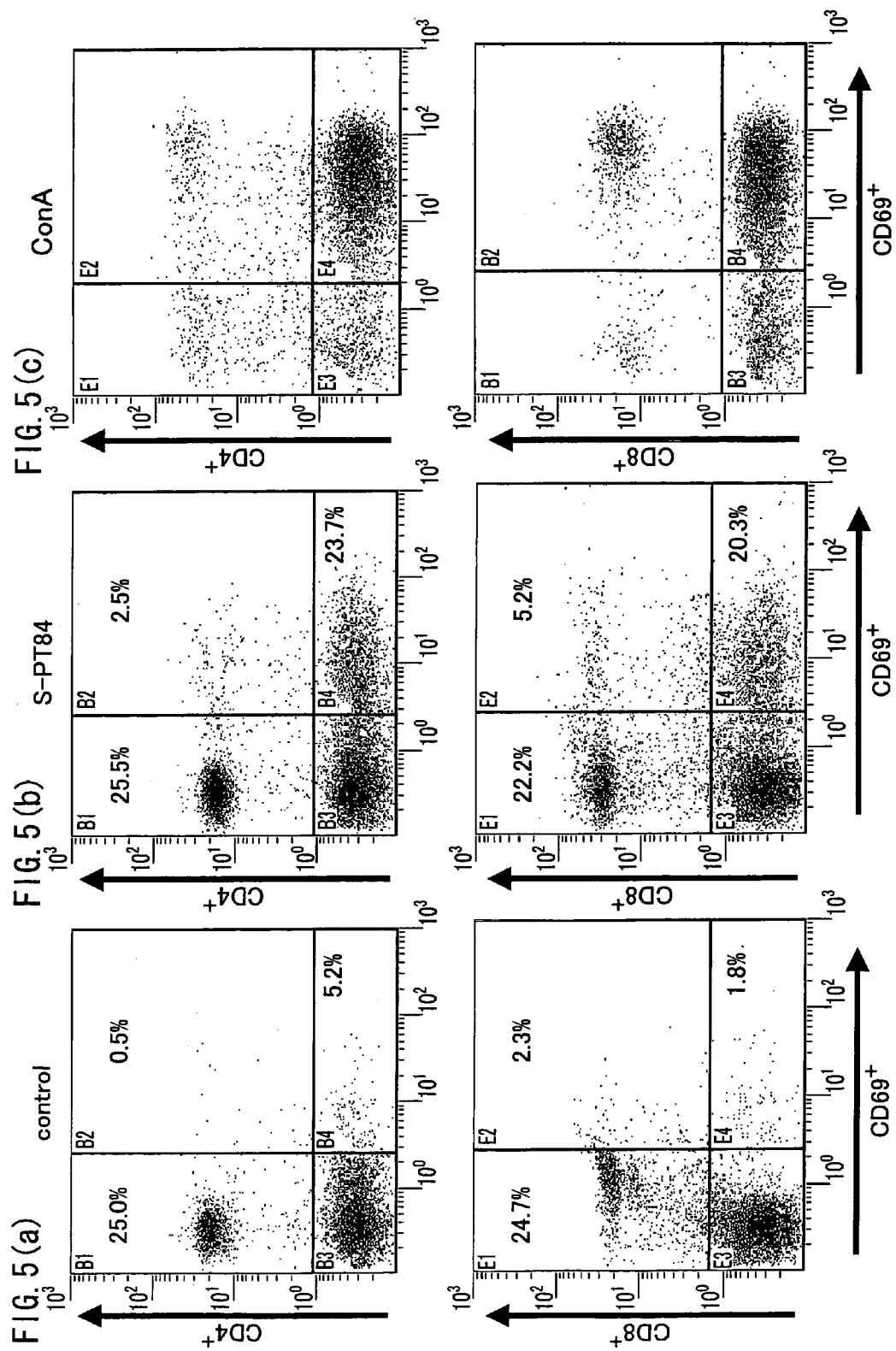

*: P<0.05 vs CY+S-PT84+S-PT84

```
SEQUENCE LISTING

<160> NUMBER OF SEQ ID NOS: 1

<210> SEQ ID NO 1
<211> LENGTH: 1519
<212> TYPE: DNA
<213> ORGANISM: Lactobacillus pentosus

<400> SEQUENCE: 1
gacgaacgct ggcggcgtgc ctaatacatg caagtcgaac gaactctggt attgattggt      60
gcttgcatca tgatttacat ttgagtgagt ggcgaactgg tgagtaacac gtgggaaacc     120
tgcccagaag cggggggataa cacctggaaa cagatgctaa taccgcataa caacttggac     180
cgcatggtcc gagtttgaaa gatggcttcg gctatcactt ttggatggtc ccgcggcgta     240
ttagctagat ggtggggtaa cggctcacca tggcaatgat acgtagccga cctgagaggg     300
taatcggcca cattgggact gagacacggc ccaaactcct acgggaggca gcagtaggga     360
atcttccaca atggacgaaa gtctgatgga gcaacgccgc gtgagtgaag aagggtttcg     420
gctcgtaaaa ctctgttgtt aaagaagaac atatctgaga gtaactgttc aggtattgac     480
ggtatttaac cagaaagcca cggctaacta cgtgccagca gccgcggtaa tacgtaggtg     540
gcaagcgttg tccggattta ttgggcgtaa agcgagcgca ggcggttttt taagtctgat     600
gtgaaagcct tcggctcaac cgaagaagtg catcggaaac tgggaaactt gagtgcagaa     660
gaggacagtg gaactccatg tgtagcggtg aaatgcgtag atatatggaa gaacaccagt     720
ggcgaaggcg gctgtctggt ctgtaactga cgctgaggct cgaaagtatg ggtagcaaac     780
aggattagat accctggtag tccataccgt aaacgatgaa tgctaagtgt tggagggttt     840
ccgcccttca gtgctgcagc taacgcatta agcattccgc ctggggagta cggccgcaag     900
gctgaaactc aaaggaattg acgggggccc gcacaagcgg tggagcatgt ggtttaattc     960
gaagctacgc gaagaacctt accaggtctt gacatactat gcaaatctaa gagattagac    1020
gttcccttcg gggacatgga tacaggtggt gcatggttgt cgtcagctcg tgtcgtgaga    1080
tgttgggtta agtcccgcaa cgagcgcaac ccttattatc agttgccagc attaagttgg    1140
gcactctggt gagactgccg gtgacaaacc ggaggaaggt ggggatgacg tcaaatcatc    1200
atgcccctta tgacctgggc tacacacgtg ctacaatgga tggtacaacg agttgcgaac    1260
tcgcgagagt aagctaatct cttaaagcca ttctcagttc ggattgtagg ctgcaactcg    1320
cctacatgaa gtcggaatcg ctagtaatcg cggatcagca tgccgcggtg aatacgttcc    1380
cgggccttgt acacaccgcc cgtcacacca tgagagtttg taacacccaa agtcggtggg    1440
gtaacctttt aggaaccagc cgcctaaggt gggacagatg attagggtga agtcgtaaca    1500
aggtagccgt aggagaacc                                                  1519
```

COMPOSITION HAVING IMMUNOREGULATING ACTIVITIES

This Nonprovisional application claims priority under 35 U.S.C. § 119(a) on Patent Application No. 159461/2004 filed in Japan on May 28, 2004, the entire contents of which are hereby incorporated by reference.

TECHNICAL FIELD

The present invention relates to a composition comprising *Lactobacillus pentosus* having immunoregulating activities.

BACKGROUND ART

Lactic acid bacteria are known to exhibit various beneficial bioactivities such as an intestine regulating activity and immunostimulating activity. Many of the Lactic acid bacteria with such beneficial bioactivities are separated from the intestinal tract or fermented dairy products obtained from animal sources. Some lactic acid bacteria from plant sources are also known to exhibit immunostimulating activities.

An example of lactic acid bacteria having immunostimulating activities is found, for example, in Patent Document 1, which discloses the *Lactobacillus plantarum* L-137 strain. Other examples include the *Lactobacillus brevis* Labre strain separated from "Suguki," which is a particular kind of traditional pickles produced in Kyoto, and the *Lactobacillus pentosus* DA74N strain separated from "Shibazuke," another kind of Kyoto pickles (see Non-Patent Documents 1, 2).

[Patent Document 1]

Japanese Laid-Open Patent Publication No. 167972/1998 (Tokukaihei 10-167972; published on Jun. 23, 1998).

[Non-Patent Document 1]

Screening of immune-enhancing Probiotics: Study of immune-enhancing effects of Lactobacilli strains by in vitro stimulation human peripheral blood mononuclear cells, Atsuko KISHI, Aoi KOKUBO, Kaoru AKATANI, Eriko OUGITANA, Setsuya FUJITA, Tsunataro KISHIDA, Pasken Journal 15. 21-26, 2002.

[Non-Patent Document 2]

The 6th Intestinal Bacteria Conference (Chonai Saikin Gakkai), May 30-31, 2002, Abstract, Kaoru AKATANI, Atsuko KISHI, Eriko OUGITANA, Aoi KOKUBO, Setsuya FUJITA, Tsunataro KISHIDA.

A wide variety of bacteria can be separated from the traditional Kyoto pickles, and it is believed that the pickles include other bacterial strains, in addition to the Labre strain, with the immunostimulating activities or other beneficial bioactivities. Among different bacterial strains separated from the pickles, *Lactobacillus plantarum* and *Lactobacillus pentosus* are most frequently separated. However, the effects of bacteria separated from the pickles have not been actively researched. In addition, since lactic acid bacteria separated from the pickles are originally contained in food, they are considered to be highly safe even if ingested by living organisms. Therefore, with the beneficial lactic acid bacteria separated from the pickles, a useful composition comprising such lactic acid bacteria can be realized.

The present invention was made in view of the foregoing problem, and an object of the invention is to provide food, drinks, medicaments, or the like that are safe and containing lactic acid bacteria, separated from traditional Kyoto pickles, having beneficial bioactivities.

DISCLOSURE OF INVENTION

The inventors of the present invention diligently worked to solve the foregoing problems. In accomplishing the invention, the inventors investigated immunoregulating activities of 16 kinds of lactic acid bacteria separated from pickles, and conducted a detailed study of immunoregulating activities of *Lactobacillus pentosus* bacteria among the separated bacteria. It was found as a result that immunoregulating activities such as immunostimulating activity and anti-allergy activity were exhibited when the *Lactobacillus pentosus* bacteria was ingested by animals with drinking water or when a suspension of the *Lactobacillus pentosus* bacteria was administered to animals.

Specifically, a composition according to the present invention comprises lactic acid bacteria which belong to *Lactobacillus pentosus* and which have a weak assimilating activity or no assimilating activity for glycerol. Preferably, the lactic acid bacteria have immunoregulating activities and are an extracellular polysaccharide-producing strain.

An example of preferable lactic acid bacteria is a *Lactobacillus pentosus* S-PT84 strain (Deposit Accession No. FERM BP-10028). The *Lactobacillus pentosus* S-PT84 strain was separated from "Shibazuke" by the inventors, and was found to possess strong immunoregulating activities. The *Lactobacillus pentosus* S-PT84 strain is also called a DS84C strain. The *Lactobacillus pentosus* S-PT84 strain (*Lactobacillus pentosus* SAM 2336) is deposited with the Deposit Accession No. FERM BP-10028 at the International Patent Organism Depositary in the National Institute of Advanced Industrial Science and Technology (AIST) located at AIST Tsukuba Central 6, 1-1, Higashi 1-chome Tsukuba-shi, Ibaraki-ken 305-8566, Japan: the strain was deposited on May 25, 2004. Therefore, a composition according to the present invention preferably comprises the *Lactobacillus pentosus* S-PT84 strain.

A composition according to the present invention comprises the lactic acid bacteria and has immunoregulating activities. Further, a composition according to the present invention comprises the lactic acid bacteria and has anti-allergy activities. In addition, a composition according to the present invention may comprise lactic acid bacteria as viable cells. The composition is useful for food, drinks, and medicaments having immunoregulating activities and/or anti-allergy activities.

For a fuller understanding of the nature and advantages of the invention, reference should be made to the ensuing detailed description taken in conjunction with the accompanying drawings.

BRIEF DESCRIPTION OF DRAWINGS

FIG. 4(*a*) through FIG. 4(*c*) are flow cytometric charts representing cytokine production from splenocytes caused by S-PT84 stimulation, in which FIG. 4(*a*) is the result using a culture medium from non-stimulated splenocytes, FIG. 4(*b*) is the result using a culture medium from heat-killed S-PT84 cells stimulated splenocytes, and FIG. 4(*c*) is the result using a culture medium from concanavalin A stimulated splenocytes.

FIG. 5(*a*) through FIG. 5(*c*) are flow cytometric charts representing effects of S-PT84 stimulation on CD4+, CD8+, and CD69+ cells, in which FIG. 5(*a*) is the result using non-stimulated splenocytes, FIG. 5(*b*) is the result using heat-killed S-PT84 cells stimulated splenocytes, and FIG. 5(*c*) is the result using concanavalin A stimulated splenocytes.

BEST MODE FOR CARRYING OUT THE INVENTION

Figure 1:
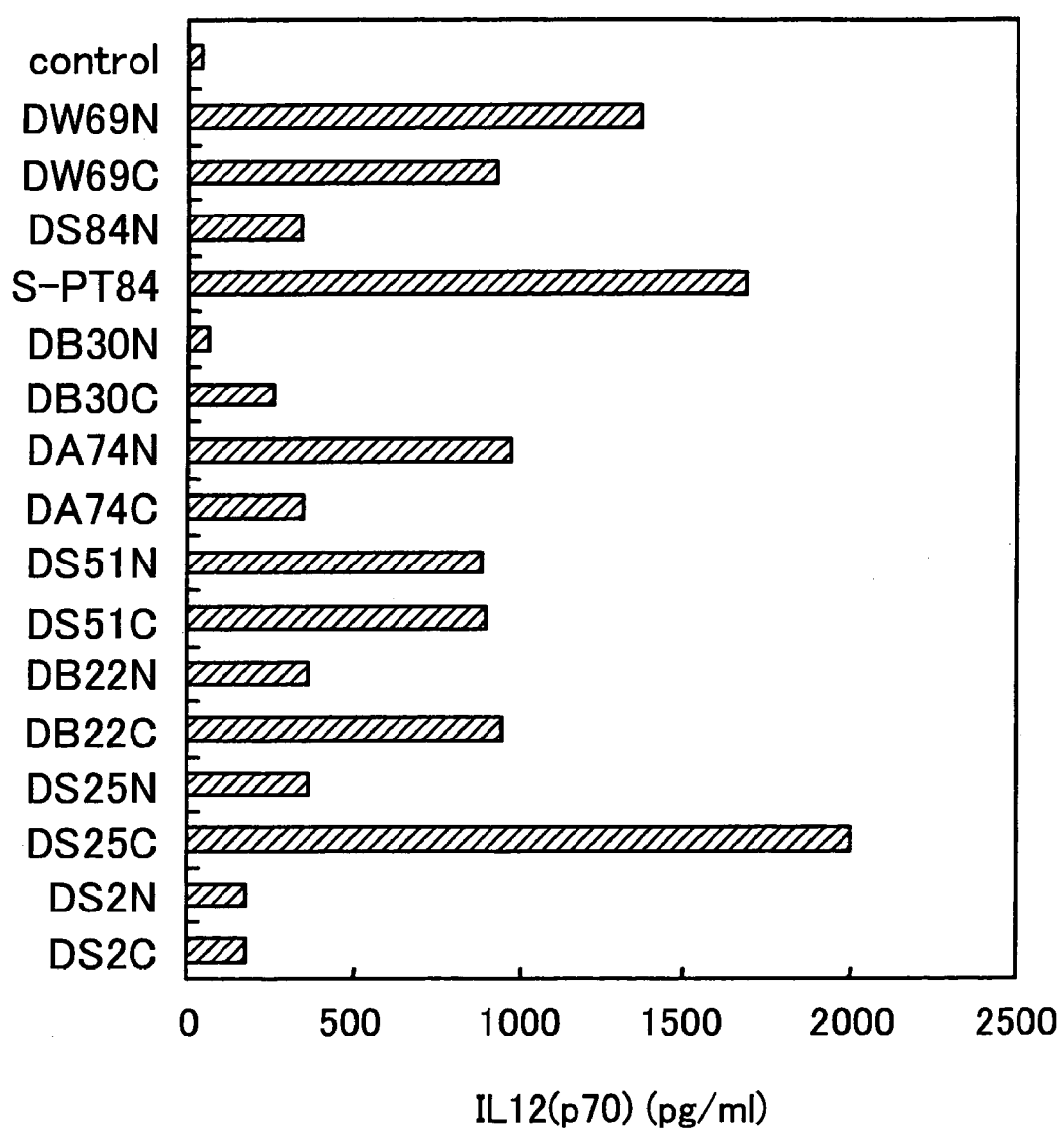
FIG. 1 is a graph representing the result of a macrophage IL-12 induction test conducted through in vitro stimulation using 16 kinds of lactic acid bacteria.

The following will describe one embodiment of the present invention. It is to be noted that the invention is not limited in any way by the following description.

Lactic acid bacteria contained in a composition according to the present invention belong to *Lactobacillus pentosus* and have a weak assimilating activity or no assimilating activity for glycerol. A composition comprising such lactic acid bacteria is highly valuable as a composition capable of exhibiting beneficial bioactivities of the lactic acid bacteria. Among such compositions, a composition having immunoregulating activities is preferable. As used herein, the term "immunoregulating activity" refers to the function of activating a steady or dropped immune function (immunostimulating activity), or the function of suppressing an excess immune function to an appropriate level (immunosuppressing activity). In addition to or instead of these activities, the term is also used to refer to the function of achieving an optimum balance between cellular immunity and humoral immunity. Non-limiting examples of immunoregulating activities include: facilitation or suppression of cytokine production; activation of lymphocytes; enhancement of NK (natural killer) activity; improvement of Th1/Th2 balance; suppression of immune reduction; and anti-allergy activity.

Further, it is preferable that lactic acid bacteria contained in a composition according to the present invention be an extracellular polysaccharide-producing strain (EPS). The property or chemical structure of EPS varies greatly from genus to genus, species to species, and strain to strain. The EPS produces capsular polysaccharides, which accumulate on the bacteria surface and is easily recognizable by Indian ink staining. The EPS-producing strain is more hydrophilic than strains that produce no EPS. This is advantageous in food applications.

A representative example of lactic acid bacteria contained in a composition according to the present invention is the *Lactobacillus pentosus* S-PT84 strain. This bacterial strain is deposited with the deposit number FERM BP-10028 at the International Patent Organism Depositary in the National Institute of Advanced Industrial Science and Technology (AIST). The *Lactobacillus pentosus* S-PT84 strain (hereinafter simply referred to as "S-PT84") will be described below.

Based on the criteria noted below, the inventors of the present invention separated and selected 16 kinds of lactic acid bacteria from "Shibazuke" (4 kinds of *Lactobacillus plantarum*, and 12 kinds of *Lactobacillus pentosus*). Specifically, 16 kinds of lactic acid bacteria were selected from the plant lactic acid bacteria if (1) they were bacilli (genus *Lactobacillus*), (2) more than one strain with the same characteristics was separated, (3) they proliferated desirably in a culture medium, and (4) they were distinct to "Shibazuke."

The 16 kinds of lactic acid bacteria were compared with respect to inducible activity of interleukin 12 (simply "IL-12" hereinafter). The result showed that the *Lactobacillus pentosus* S-PT84 strain yielded the highest concentration of serum IL-12 when intraperitoneally administered to mice.

Detailed studies of S-PT84 immunoregulating activities led to the following findings.

(1) When processed in vitro in the splenocytes prepared from mice, the S-PT84 induced the production of IFN-γ (interferon γ) and TNF-α (tumor necrosis factor α) of the Th1-type cytokine, and thereby increased the number of CD4+CD69+cells and CD8+CD60+cells. That is, the S-PT84 functioned to activate the helper T cells or killer T cells.

(2) When intraperitoneally administered to mice, the S-PT84 enhanced the NK activity of the hepatic lymphocytes. In addition, the S-PT84 increased the number of CD8+cells and CD8+CD69+cells, and thereby enhanced the cellular immunity.

(3) When orally administered to mice, the S-PT84 raised the concentration of serum IL-12, increased the number of CD4+, CD8+, and CD3+ cells in the spleen, and thereby enhanced the NK activity of the splenocytes. As a result, the Th1/Th2 balance in the splenocytes became Th 1 dominant.

(4) When orally administered to mice, the S-PT84 suppressed a weight loss caused by administration of cyclophosphamide, and suppressed immune response reduction.

(5) When orally administered to mice, the S-PT84 suppressed increase of ovalbumin (OVA)-specific IgE and total IgE, even when sensitized with OVA.

(6) When orally administered to mice, the S-PT84 suppressed stress-induced reduction of NK activity.

From these findings, the S-PT84 was confirmed to be a strain with immunoregulating activities.

Table 1 below shows bacterial characteristics of the S-PT84.

TABLE 1

| Cell morphology | Bacillus |
|---|---|
| Spore | Absent |
| Gram staining | Positive |
| Mobility | Absent |
| End spore | Absent |
| Catalase reaction | Negative |
| Growth at 15° C. | Good |
| Growth at 45° C. | No growth |
| Sugar assimilating activity (Positive: +, Negative: −, Weakly positive: w) | |
| D-arabinose | − |
| L-arabinose | + |
| Ribose | + |
| D-xylose | + |
| L-xylose | − |
| Galactose | + |
| Glucose | + |
| Fructose | + |
| Mannose | + |
| Raffinose | w |
| Mannitol | + |
| Sorbitol | + |
| Cellobiose | + |
| Lactose | + |
| Melibiose | + |
| Trehalose | + |
| Glycerol | w |
| Xylitol | + |

*Lactobacillus pentosus* is generally known to have a strong assimilating activity for glycerol. However, the S-PT84 had a weak assimilating activity for glycerol, as shown in Table 1. Thus, the S-PT84 was found to be different from any other known *Lactobacillus pentosus*.

After extracting DNA from S-PT84, a total of about 500 bp in the entire region of the 16SrRNA gene was sequenced using the Microseq Full Gene 16S rDNA kit (Applied Biosystems). The 16SrRNA gene sequence (SEQ ID NO: 1) was 100% homologous to the 16SrRNA gene sequence of *Lactobacillus pentosus* JCM$^T$ (D79211). From this, the S-PT84 was identified as *Lactobacillus pentosus*.

The S-PT84 is more hydrophilic than bacteria that produce no EPS, and has essentially no adherence to a plastic surface. Further, the S-PT84 has essentially no agglomeration activity for yeasts.

A composition according to the present invention comprises lactic acid bacteria which belong to *Lactobacillus pentosus* and which have a weak assimilating activity or no assimilating activity for glycerol. A composition according to the present invention preferably has immunoregulating activities or anti-allergy activities. It would be more advantageous if the composition exhibits both immunoregulating activities and anti-allergy activities.

A composition according to the present invention is advantageously usable in the form of food, drinks, or medicaments having immunoregulating activities and/or anti-allergy activities. In other words, the composition can be suitably used as a pharmaceutical composition having immunoregulating activities and/or anti-allergy activities.

The lactic acid bacteria may be contained in a composition either directly (viable or dead), or in the form of an inclusion or processed cells, for example. Viable cells may be obtained from an inclusion of lactic acid bacteria such as a broth of lactic acid bacteria. Dead cells may be obtained by subjecting viable cells to heat, UV irradiation, or a formalin treatment, for example. The viable cells or dead cells may be ground or crushed into processed cells.

That is, a composition according to the present invention includes at least one of: lactic acid bacteria; an inclusion of lactic acid bacteria; and processed cells of lactic acid bacteria. Examples of lactic acid bacteria include viable cells, wet cells, and dried cells. The lactic acid bacteria inclusion may be a suspension of lactic acid bacteria, a culture medium of lactic acid bacteria (including lactic acid bacteria, supernatant, and medium itself), a broth of lactic acid bacteria (obtained by removing a solid component from the culture medium), or fermented milk of lactic acid bacteria (lactic acid bacteria beverage, sour milk, yoghurt, etc.). The processed cells of lactic acid bacteria may be, for example, ground cells, crushed cells, liquefied cells (extract, etc.), concentrated cells, paste cells, dried cells (spray-dried cells, freeze-dried cells, vacuum-dried cells, drum-dried cells), or diluted cells. The S-PT84 contained in a composition according to the present invention is separated from the fermented "Shibazuke," and as such a composition comprising the product of fermented fruits, vegetables, or cereals with S-PT84 is also suitable as one embodyment of a composition according to the present invention. It should be noted that a composition comprising S-PT84 is safe because S-PT84 is separated from food, as described above.

It is preferable that a composition according to the present invention be used as food, drinks, medicaments, or the like. More specifically, the composition is preferably used as a pharmaceutical composition having immunoregulating activities. When used as food or drink, it is preferable that the composition be provided as health food having immunoregulating activities. Further, the composition may be combined with conventional sweeteners, acidifiers, vitamins, or various other components to provide user-selective products. For example, the composition may be provided in the form of a tablet, a capsule, a health drink, a dairy product such as yoghurt or lactic acid bacteria beverage, a flavor enhancer, processed food, dessert, or confectionary.

Examples of medicaments include an immunostimulant and an anti-allergic drug. The composition may be prepared into a medicament as an active component in combination with conventional auxiliaries commonly used in the field of drug preparation. Examples of such auxiliaries include: an excipient, a binder, a disintegrator, a lubricant, a fragrance, a solubilizing agent, a suspending agent, and a coating agent. The form of dosage is not particularly limited. For example, the medicament may be in the form of a tablet, a capsule, a granule, a powder, a syrup, a suppository, or an injection. The administration route of the medicament is not particularly limited either. For example, oral administration, rectal administration, and transintestinal administration are available.

EXAMPLES

[Lactic Acid Bacteria Strains Used]

Four kinds of *Lactobacillus plantarum* and twelve kinds of *Lactobacillus pentosus* were separated from "Shibazuke," a kind of traditional Kyoto pickles. These bacterial strains were compared with respect to inducible activity of interleukin 12 (IL-12), in order to select strains with good Th1-type immunostimulating activity. For each strain used, Table 2 lists names of strain and species, and the presence or absence of EPS. From the result of comparison for IL-12 inducible activity, the activity of DS84C strain (S-PT84) was found to be particularly strong. As such, subsequent experiments were conducted only for S-PT84.

TABLE 2

| Strain | Species | Extracellular Polysaccharide (EPS) |
|---|---|---|
| DW69N | Lactobacillus. pentosus | − |
| DW69C | Lactobacillus. pentosus | + |
| DS84N | Lactobacillus. pentosus | − |
| DS84C (S-PT84) | Lactobacillus. pentosus | + |
| DB30N | Lactobacillus. pentosus | − |
| DB30C | Lactobacillus. pentosus | + |
| DA74N | Lactobacillus. pentosus | − |
| DA74C | Lactobacillus. pentosus | + |
| DS51N | Lactobacillus. pentosus | − |
| DS51C | Lactobacillus. pentosus | + |
| DB22N | Lactobacillus. plantarum | − |
| DB22C | Lactobacillus. plantarum | + |
| DS25N | Lactobacillus. pentosus | − |
| DS25C | Lactobacillus. pentosus | + |
| DS2N | Lactobacillus. plantarum | − |
| DS2C | Lactobacillus. plantarum | + |

[IL-12 Induction by In Vitro Stimulation]

First, 4.05% thioglycolate was intraperitoneally administered to BALB/c mice (7 weeks of age, male). After 4 days, intraperitoneal macrophages were collected with PBS, and adjusted to $2\times10^6$ cells/mL using RPMI medium containing 10% FBS. The culture was inoculated on a 24-well plate (0.5 ml/well). Then, heat-killed cells (10 μg/mL) of each strain were added to each well, and, after 24 hour incubation, the IL-12 concentration of the supernatant was measured. Since the active form of IL-12 is P70 combining two subunits p35 and p40, the concentration of IL-12 (p70) was measured. For the measurement of IL-12, the OptEIA mouse IL-12 ELISA kit (BD Pharmingen) was used.

The results are shown in FIG. 1. As is clear from FIG. 1, the inducible activity of IL-12 varied greatly even among the strains of the same species or same parental strain. Among these strains, the activity was particularly high in DW69N, S-PT84 (DS84C), and DS25C.

[IL-12 Induction by In Vivo Stimulation]

Figure 2:
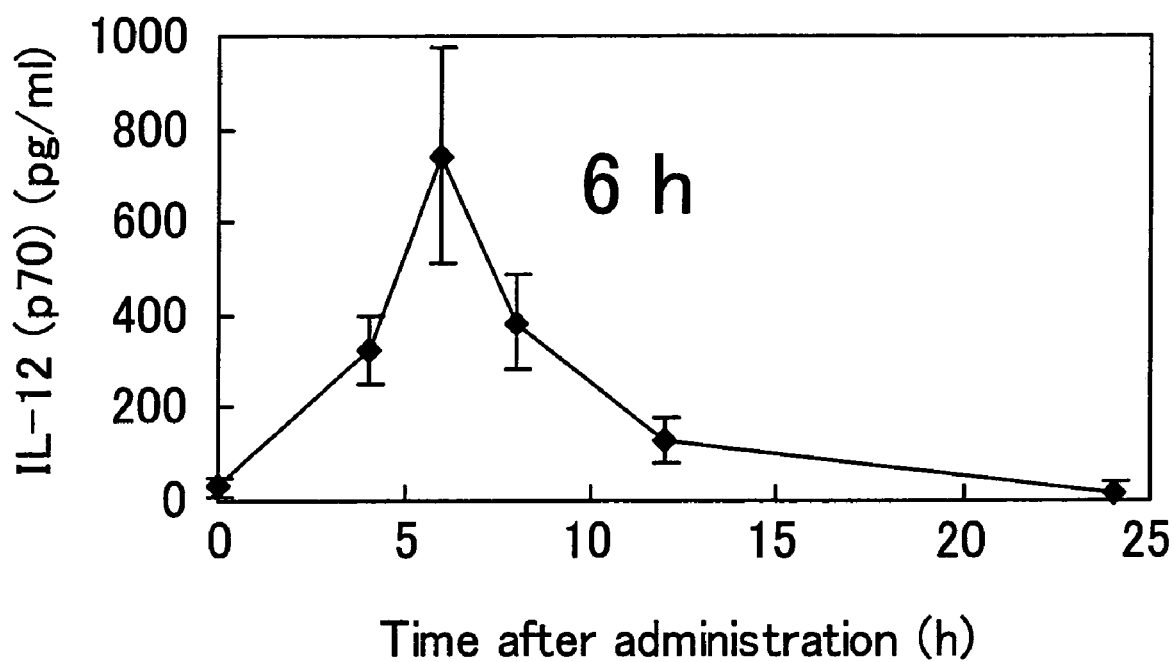
FIG. 2 is a graph representing changes in serum IL-12 concentration in response to intraperitoneal administration of S-PT84.

A suspension (solvent; saline solution) of heat-killed cells (500 μg/0.2 mL/mouse) of each strain was intraperitoneally administered to BALB/c mice (7 weeks of age, male). After 6 hours, the cervical was dislocated and the blood was collected from the heart. For the control mice, the same amount of saline solution was administered. The blood was collected 6 hours after the administration because a preliminary analysis using S-PT84 had revealed that the peak concentration of serum IL-12 occurs 6 hours after the administration of dead cells (FIG. 2). After the blood was collected, the serum was collected by centrifugation. The IL-12 concentration in the serum was measured with the OptEIA mouse IL-12 ELISA kit (BD Pharmingen).

Figure 3:
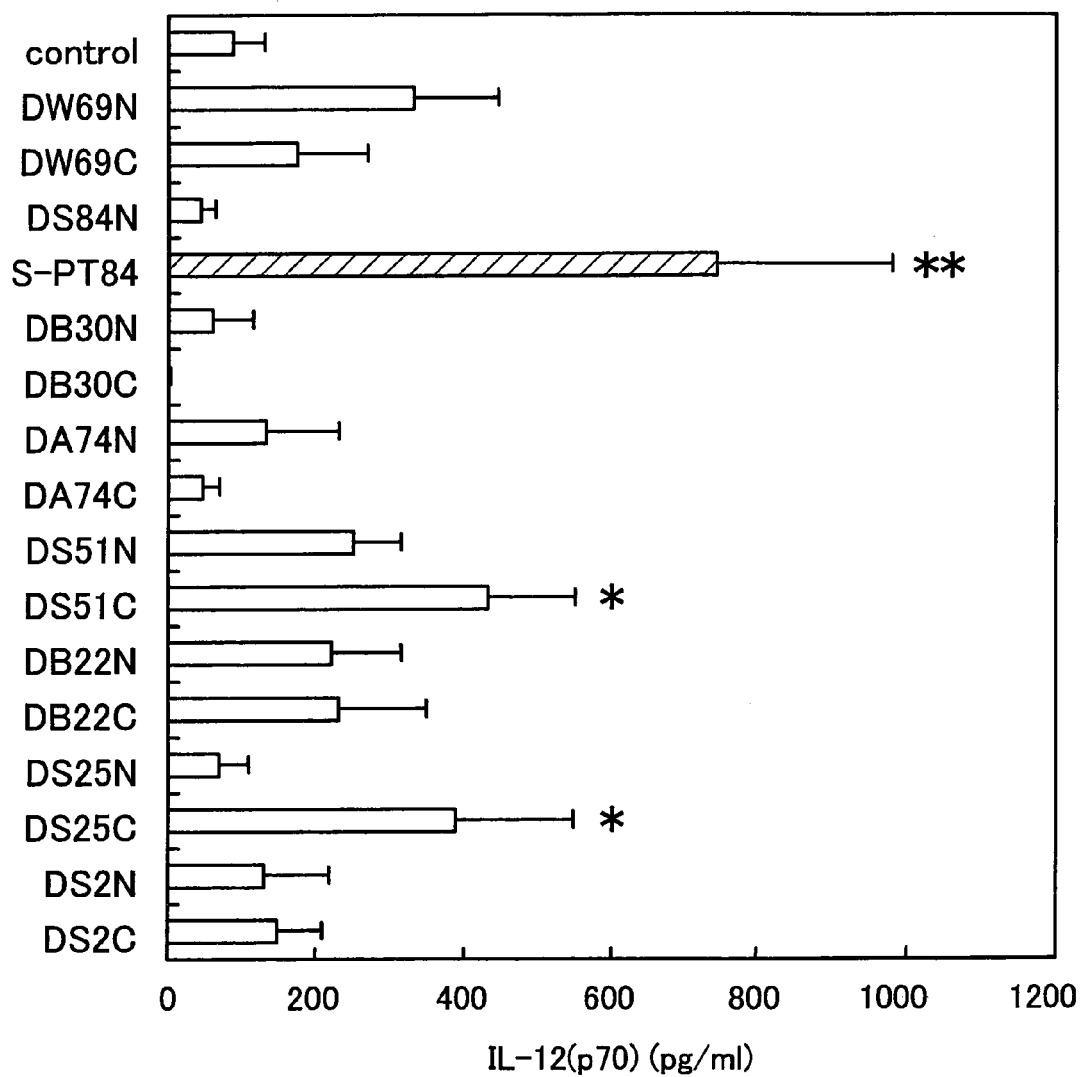
FIG. 3 is a graph representing the results of measurement on mouse serum IL-12 concentration in response to intraperitoneal administration of 16 kinds of lactic acid bacteria.

The results are shown in FIG. 3. As is clear from FIG. 3, the concentration of serum IL-12 was significantly high for samples to which S-PT84 (DS84C), DS51C, and DS25C were administered, compared with the control. Since the S-PT84 (DS84C) had the highest concentration, only this strain was used in subsequent experiments.

[Effects S-PT84 on Lymphocytes]

Spleens were removed from BALB/c mice (7 weeks of age, male), and splenocytes were prepared according to ordinary method. The splenocytes were cultured for 24 hours in a medium containing (1 μg/ml) of heat-killed S-PT84 cells. As a control, the splenocytes were cultured alone in a medium (control). As another control, the splenocytes were also cultured in a medium with the addition of concanavalin A (2.5 μg/mL) (Con A). In order to determine the type of cytokine produced by the stimulus of the S-PT84 dead cells, the cytokine concentration in the supernatant of each medium was measured using the CBAkit (BD Pharmingen). The splenocytes were collected and labeled with the fluorescent-labeled anti-CD4 antibody (CY-CHCROME™ label, BD bioscience), anti-CD8 antibody (FITC label, Immunotech), and anti-CD69 antibody (PE label, BD bioscience), and the respective proportions of CD4-, CD8-, and CD69-positive cells were measured with the flow cytometry (Beckman Coulter).

FIG. 4 depicts the result of cytokine production. FIG. 4(a) is the result for the control in which the medium was used alone, FIG. 4(b) is the result for S-PT84 in which the S-PT84 dead cells were added to the medium, and FIG. 4(c) is the result for Con A in which concanavalin A was added to the medium. As is clear from FIG. 4, the S-PT84 stimulus produced IFN-γ (interferon γ) and TNF-α (tumor necrosis factor α), which were not observed in the control. These cytokines were Th1-type cytokines. It was therefore believed that the S-PT84 specifically induced Th1-type cytokines. The Th2-type cytokines such as IL-4 or IL-5 were not produced at all. With the concanavalin A stimulation, another type of Th1-type cytokine, IL-2 (interleukin 2), was produced.

FIG. 5 shows how the CD4+, CD8+, and CD69+ cells were affected. FIG. 5(a) is the result for the control in which the medium was used alone. FIG. 5(b) is the result for the S-PT84 in which the S-PT84 dead cells (1 μg/mL) were added to the medium. FIG. 5(c) is the result for Con A in which concanavalin A was added to the medium. In FIG. 5, the directions of arrows indicate increasing numbers of positive cells for each surface antigen. As is clear from FIG. 5, the helper T cells and killer T cells were activated by the S-PT84.

[Changes in Hepatic Lymphocytes after Intraperitoneal Administration of S-PT84]

A suspension (solvent; saline solution) of heat-killed S-PT84 cells (500 μg/0.2 mL/mouse) was administered intraperitoneally to C57BL/6 mice (7 weeks of age, male). After 24 hours, liver was removed, and hepatic lymphocytes were prepared by centrifugation. As a control, only the saline solution was intraperitoneally administered. The NK activity of the hepatic lymphocytes was measured by a PINK method. The PINK method is a method for calculating the cytotoxic activity of the mouse lymphocytes according to the following procedure. First, a target cell Yac-1 is labeled with 3,3'-dioctadecyloxacarbocyanine perchlorate (Dio), which is a hydrophobic fluorescent dye for labeling a membrane. Then, the nucleus of the dead cell is double stained with propidium iodide (PI), which is a membrane-impermeable nucleic acid binding fluorescent dye. The Yac-1 cells were detected with the flow cytometry, using Dio simple staining for uninjured cells, and double staining for injured cells. Further, the other hepatic cells were labeled with the fluorescent-labeled anti-CD4 antibody (CY-CHCROME™ label, BD bioscience), anti-CD8 antibody (FITC label, Immunotech), and anti-CD69 antibody (PE label, BD bioscience), and the respective proportions of CD4-, CD8-, and CD69-positive cells were measured with the flow cytometry (Beckman Coulter).

Figure 6:
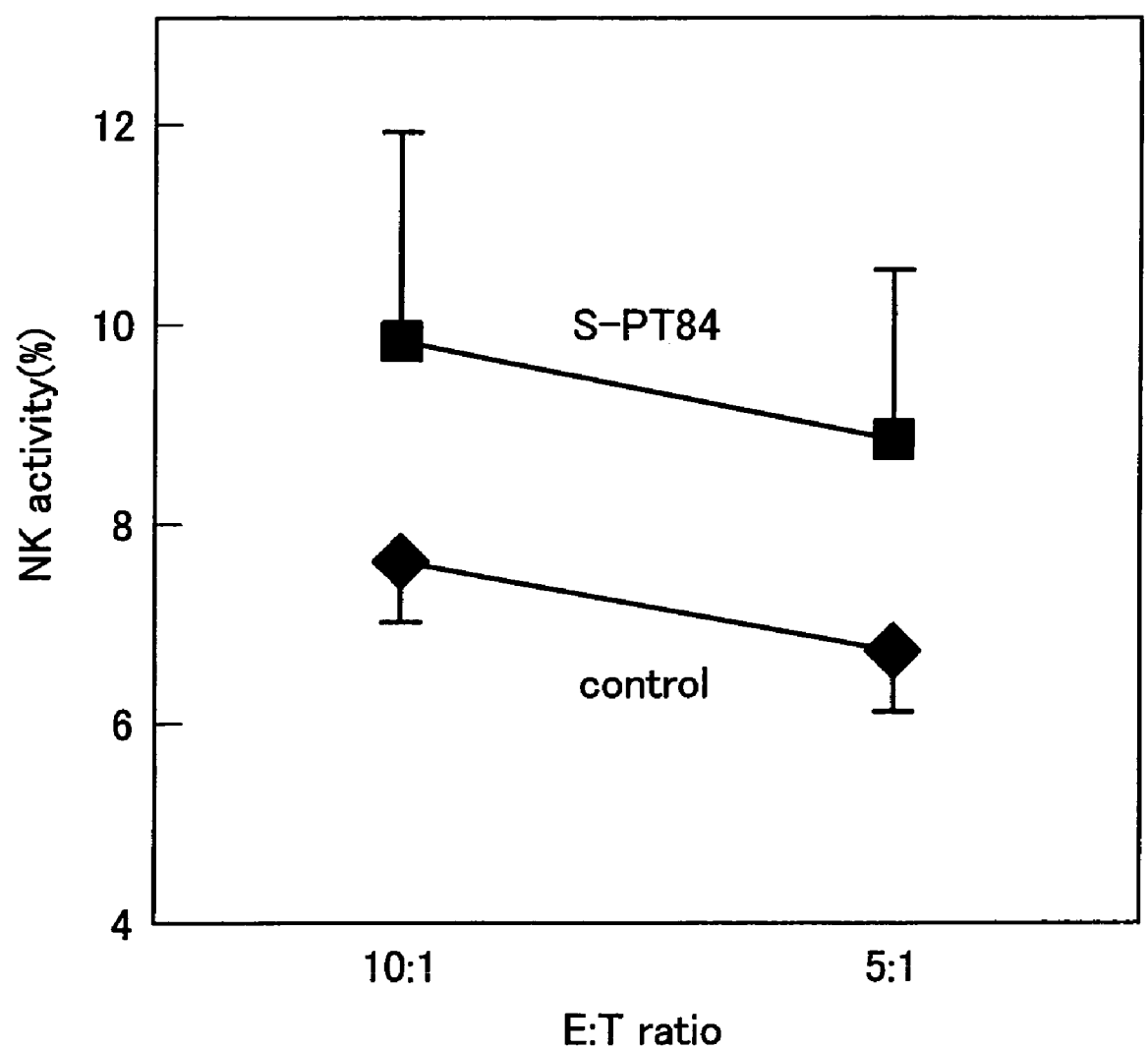
FIG. 6 is a graph representing the result of measurement on NK activity of hepatic lymphocytes in response to intraperitoneal administration of S-PT84.

FIG. 6 shows the result of NK activity measurement. In FIG. 6, the NK activity (%) indicates cellular cytotoxicity of the mouse hepatic lymphocytes against Yac-1, and E:T ratio indicates the value of the number of reacted hepatic lymphocytes versus the number of Yac-1 cells. As is clear from FIG. 6, the NK activity of the hepatic lymphocytes prepared from mice to which the S-PT84 was intraperineally administered was clearly higher than that of the control.

Figures 7A, 7B:
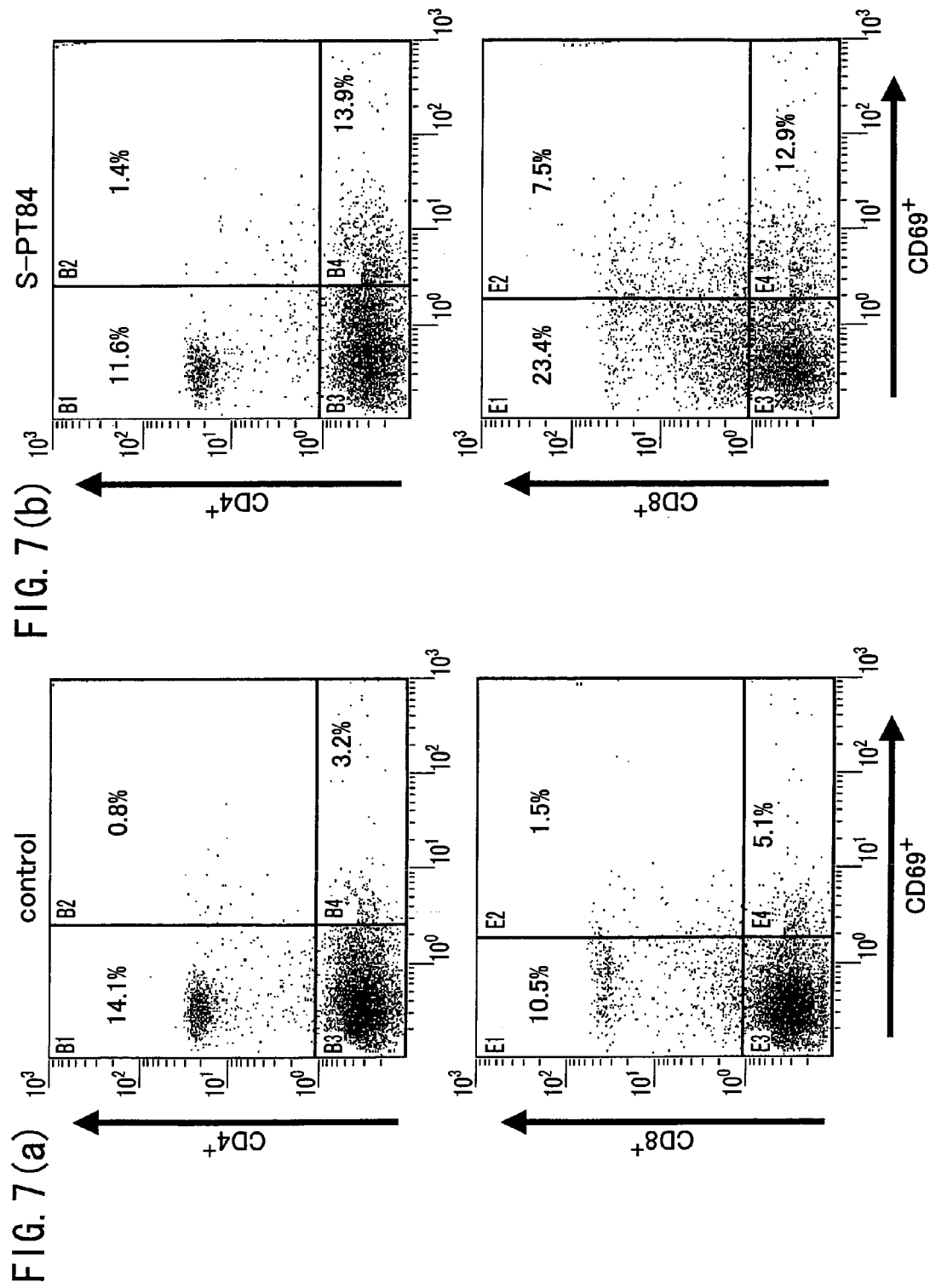
FIG. 7(*a*) and FIG. 7(*b*) are flow cytometric charts representing effects of S-PT84 intraperitoneal administration on CD4+, CD8+, and CD69+ cells of hepatic lymphocytes, in which FIG. 7(*a*) is the result for the control, and FIG. 7(*b*) is the result with S-PT84 administration.

FIG. 7 shows the results for CD4+, CD8+, and CD69+ cells, in which FIG. 7(a) is the result for the control, and FIG. 7(b) is the result with the administration of S-PT84. Further, in FIG. 7, the directions of arrows indicate increasing numbers of positive cells for each surface antigen. As is clear from FIG. 7, the number of CD8+ cells, as well as CD8+CD69+ cells, clearly increased. It was therefore found that the administration of S-PT84 increases the number of the killer T cells in the liver, as well as the number of active killer T cells.

[Th1/Th2 Balance Regulating Activity by Oral Administration of S-PT84]

Six BALB/c mice (7 weeks of age, male) were allowed to drink S-PT84 (dead cells)-containing water for a week (equivalent of 2 mg/day). As a control group, six mice with no S-PT84 were used. After one week, blood was collected from the heart, and spleen was removed. The serum was collected from the blood by centrifugation, and the IL-12 concentration in the serum was measured using the OptEIA mouse IL-12 ELISA kit (BD Biosciences). From the spleen, splenocytes were prepared by ordinary method, and the number of the CD4+, CD8+, and CD3+ cells in the splenic lymphocytes were counted (measurement was made with the flow cytometry, using labeled antibodies of the respective cells). Further, the NK activity was measured by the PINK method. A measurement of Th1/Th2 ratio was also carried out (2.5 µg/ml of concanavalin A was allowed to act on $5 \times 10^6$ mouse splenocytes for 24 hours, and the concentrations of resulting IL-4 and IFN-γ in the supernatant were measured). The Th1/Th2 ratio was obtained by dividing the IFN-γ concentration by Il-4 concentration.

Figure 8:
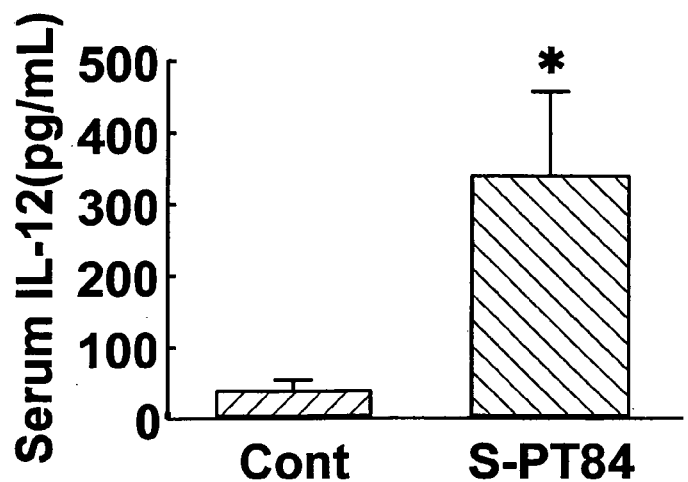
FIG. 8 is a graph representing the result of measurement on serum IL-12 concentration in mice to which S-PT84 was orally administered.

FIG. 8 shows the result of measurement of serum IL-12 concentration. As is clear from FIG. 8, the concentration of serum IL-12 in the S-PT84-orally administered mice was significantly higher than that of the control group (Cont).

Table 3 below represents the result of measurement of CD4+, CD8+, and CD3+ cells. As is clear from FIG. 3, the splenic lymphocyte T subset had a tendency to increase.

TABLE 3

| Cell ($\times 10^6$ cells) | Control | S-PT84 | Ratio |
| --- | --- | --- | --- |
| Spleen | 68.3 ± 3.9 | 128.0 ± 42.0 | 1.9 |
| CD4+ | 15.1 ± 0.7 | 36.2 ± 11.2 | 2.4 |
| CD8+ | 4.6 ± 0.4 | 9.7 ± 11.2 | 2.1 |
| CD3+ | 27.6 ± 1.6 | 61.0 ± 19.8 | 2.2 |

Figure 9:
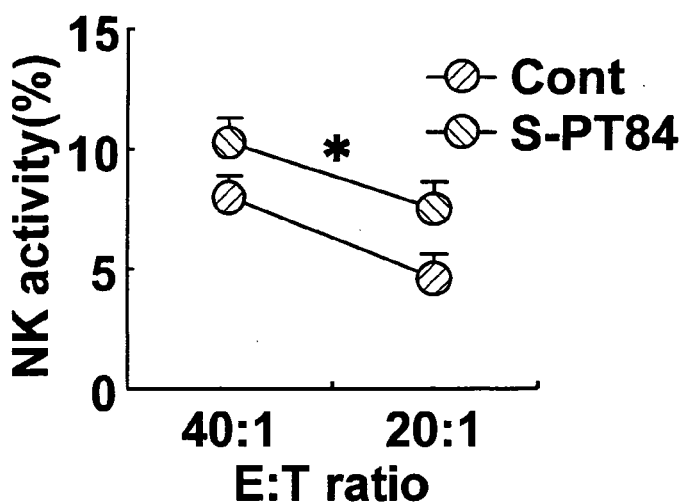
FIG. 9 is a graph representing the result of measurement of splenic NK activity of mice to which S-PT84 was orally administered.

FIG. 9 shows the result of measurement of NK activity. In FIG. 9, the NK activity (%) indicates cytotoxicity of the mouse splenocytes against Yac-1, and E:T ratio indicates the value of the number of reacted splenocytes versus the number of Yac-1 cells. As is clear from FIG. 9, the NK activity of the splenocytes prepared from the mice to which S-PT84 was orally administered was significantly higher than that of the control group (Cont).

Figure 10:
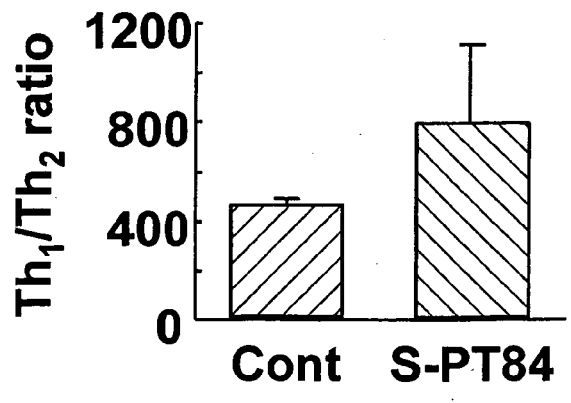
FIG. 10 is a graph representing the result of measurement of Th1/Th2 ratio in splenocytes of mice to which S-PT84 was orally administered.

FIG. 10 shows the result of measurement of Th1/Th2 ratio. As is clear from FIG. 10, the splenocytes prepared from mice to which the S-PT84 was orally administered had a considerably large proportion of Th1 cytokine as compared with the control group (Cont).

As described above, the Th1-type cytokine was induced in mice to which the S-PT84 was orally administered. As a result, the Th1/Th2 balance shifted to Th1 dominant, and the NK activity increased as a result. This proved the Th1/Th2 balance adjusting activity and immunostimulating activity of the S-PT84.

[Effects on Change of the Weight of Cyclophosphamide-administered Mice]

Twenty BALB/c mice (7 weeks of age, male) were divided into two groups of an almost equal average weight, so as to provide an S-PT84 administered group and an S-PT84 non-administered group (control group). The S-PT84 administered group was allowed to drink S-PT84 (dead cells)-containing water for 22 days (equivalent of 2 mg/day). After 8 days from the start of administration, 200 mg/kg of cyclophosphamide (CY) (antitumor chemotherapeutic drug, alkylating agent) was intraperitoneally administered to all individuals. A weight of each individual was measured on the 1st, 2nd, 3rd, 5th, 8th, 12th, and 15th days from the CY administration.

Figure 11:
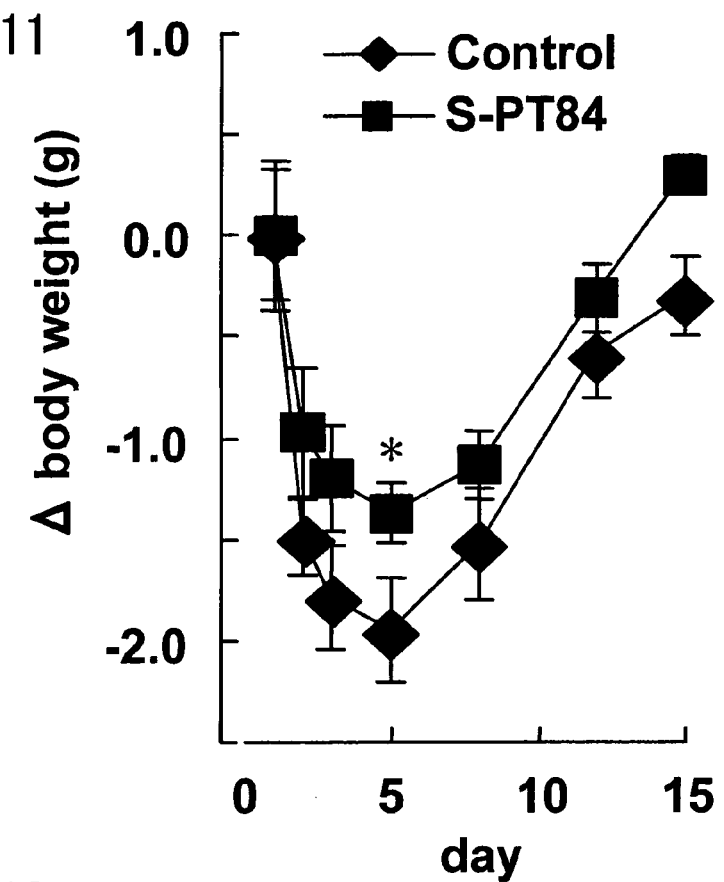
FIG. 11 is a graph representing changes in the weight of mice to which S-PT84 was orally administered, in response to cyclophosphamide administration.

FIG. 11 shows changes in average body weight in the both groups. As is clear from FIG. 11, a body weight loss caused by the CY administration was suppressed in the S-PT84 administered group, as compared with the control group (Control).

[Effects on IL-12 Production in Cyclophosphamide-administered Mice]

BALB/c mice (7 weeks of age, male) were divided into 5 groups: an untreated group (5 mice); an S-PT84 non-administered and CY non-administered group (10 mice); an S-PT84 non-administered and CY administered group (10 mice); an S-PT84 administered and CY non-administered group (10 mice); and an S-PT84 administered and CY administered group (11 mice). The two S-PT84 administered groups were allowed to drink S-PT84 (dead cells)-containing water for 12 days (equivalent of 2 mg/day). After 7 days from the start of administration, 200 mg/kg of cyclophosphamide (CY) (antitumor chemotherapeutic drug, alkylating agent) was intraperitoneally administered to the CY administered groups. After 5 days from the CY administration, a suspension (solvent; saline solution) of heat-killed cells of S-PT84 (500 µg/0.2 ml/mouse) was intraperitoneally administered to the mice of all groups except for the untreated group. Six hours after the administration of S-PT84 dead cells, blood was collected from the heart in all individuals, including those in the untreated group. From the collected blood, the serum was collected by centrifugation, and the IL-12 concentration in the serum was measured with the OptEIA mouse IL-12 ELISA kit (BD Pharmingen).

Figure 12:
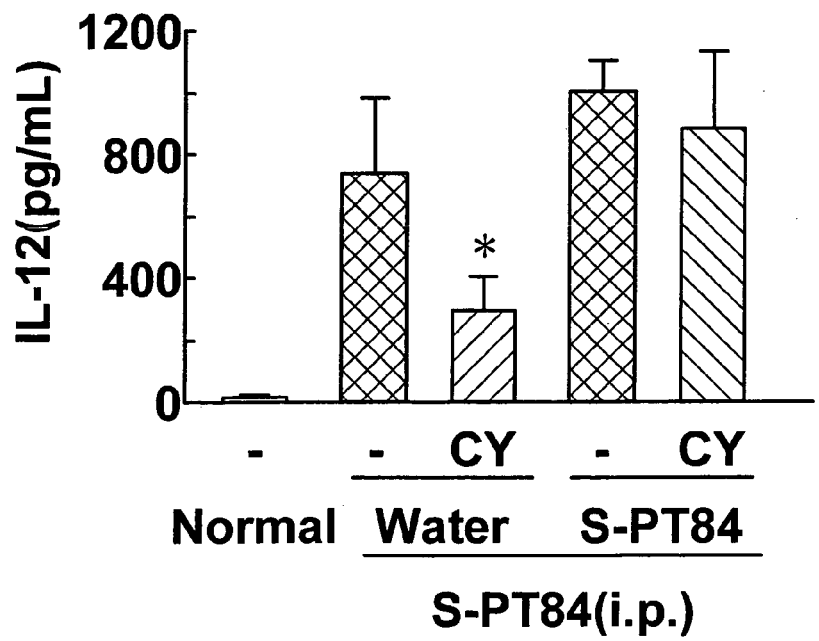
FIG. 12 is a graph representing the result of measurement of serum IL-12 concentration in mice to which S-PT84 was orally administered, in response to cyclophosphamide administration.

The results are shown in FIG. 12. As is clear from FIG. 12, the CY administration in the S-PT84 non-administered group reduced the IL-12 concentration in the serum by a considerable amount. On the other hand, in the S-PT84 administered group, the reduction of IL-12 concentration in the serum caused by the CY administration was suppressed significantly, and the IL-12 concentration in the serum was almost equal to that of the control group.

From these results, it was proved that the S-PT84 has the ability to suppress a weight loss and immune reduction caused by CY. In other words, the immunostimulating activity of the S-PT84 was confirmed.

[Analysis of Anti-allergy Activities]

Thirty-six BALB/c mice (7 weeks of age, male) were divided into four groups: an untreated group (5 mice); a control group (10 mice); an S-PT84 group (11 mice); and a dexamethasone administered group (10 mice). The S-PT84 group was allowed to drink S-PT84 (dead cells)-containing water for 7 weeks (equivalent of 2 mg/day). To the Dex administered group, 0.5 mg/kg of S-PT84 was forcibly administered for 7 weeks by oral administration. The untreated group and control group were allowed to drink tap water for 7 weeks. Note that, the Dex is a steroid drug with anti-allergenic and anti-inflammatory activities, and was used as a positive control drug. One week and two weeks after the S-PT84 uptake or Dex administration, a mixture containing 20 µg of ovalbumin (OVA) and 2 mg of aluminum hydroxide gel was intraperitoneally administered to the mice of all groups except for the untreated group. From the second administration (0 week) to the 5th week, blood was collected every week a total of 6 times from all individuals, and an OVA-specific IgE concentration was measured. The measurement of OVA-specific IgE concentration in the serum was carried out according to the ELISA method, using a modified OptEIA mouse IgE ELISA kit (BD Pharmingen) in which OVA was coated instead of the capturing antibody. Using the blood sample from the third week, total IgE was measured. The measurement of total IgE was carried out according to the ELISA method, using the OptEIA mouse IgE ELISA kit.

Figure 13:
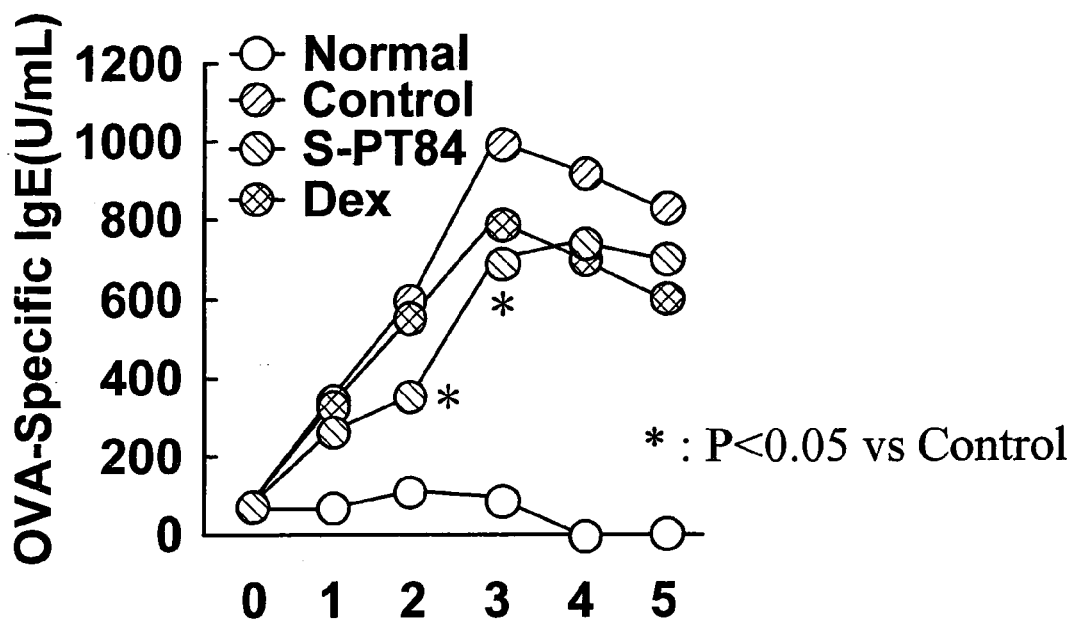
FIG. 13 is a graph representing changes in OVA-specific IgE concentration in mice to which S-PT84 was orally administered.
Figure 14:
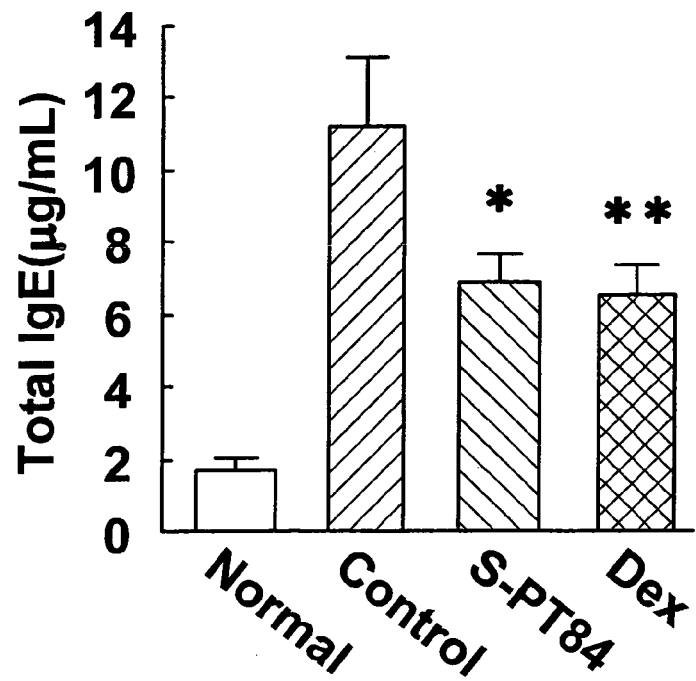
FIG. 14 is a graph representing the result of measurement of total IgE concentration 3 weeks after OVA administration in mice to which S-PT84 was orally administered.

FIG. 13 shows changes in OVA-specific IgE concentration on the $3^{rd}$ week of the experiment start. FIG. 14 shows the result of measurement on total IgE concentration. As is clear from FIG. 13, the S-PT84 group significantly suppressed the increase of OVA-specific IgE concentration as compared with the control group (control). In the Dex group, the result was not significantly different from the control group, though some suppressing effect was observed. Further, as is clear from FIG. 14, the S-PT84 group and Dex group significantly suppressed increase of total IgE concentration as compared with the control group (control).

It became clear from these results that the S-PT84 had an anti-allergy activity.

[Analysis of Suppressing Effect on Stress-induced Immune Reduction]

Nine C57BL/6 mice (6 weeks of age, male) were divided into three groups of an almost equal average weight, so as to provide a control group (3 mice), a stressed group (3 mice), and an S-PT84 administered and stressed group (3 mice). The S-PT84 administered group was allowed to drink S-PT84 (dead cells)-containing water for 7 days (equivalent of 2 mg/day). On the eighth day of the administration, a total of 6 mice in the stressed group and the S-PT84 administered and stressed group were immersed in water, placed in a 50 ml polyethylene tube whose tip had an air vent, and restricted for 24 hours. The control group was deprived of food and water. From each animal, the spleen was removed, and splenic lymphocytes were prepared for the measurement of NK activity.

Figure 15:
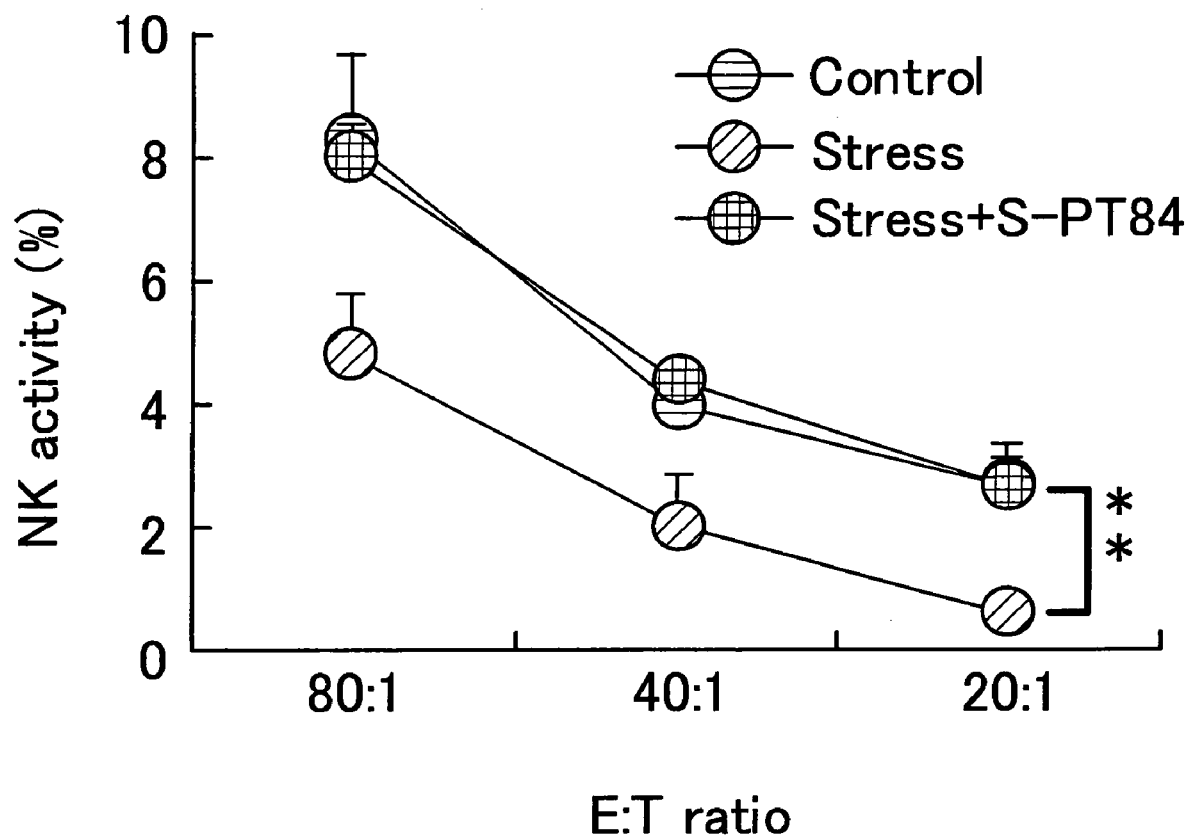
FIG. 15 is a graph representing NK activity reduction suppressing effects in mice to which S-PT84 was orally administered and which were placed under stress.

FIG. 15 shows the result of measurement on NK activity. The stressed group showed a significant drop in NK activity compared with the control group. The S-PT84 administered and stressed group maintained NK activity comparable to that of the control group, i.e., the NK activity level was significantly higher than that of the stressed group. This proved that the S-PT84 had the activity of suppressing stress-induced immune reduction.

[Difference in Immunostimulating Activity Between Dead Cells and Viable Cells]

The immunostimulating activities were compared between dead cells and viable cells of the lactic acid bacteria. For the comparison, the lactic acid bacteria that increased the mouse serum IL-12 concentration in response to intraperitoneal administration as shown in FIG. 3 were used.

Suspensions of 4 kinds of lactic acid bacteria (DB22C, DS51C, DS2C and DS84C (S-PT84)), both in the form of heat-killed cells and viable cells, were prepared (each weighing 500 µg ($2.5 \times 10^8$/0.2 mL/mouse)). The suspensions were intraperitoneally administered to BALB/c mice (7 weeks of age, male). After 6 hours, the cervical was dislocated and the blood was collected from the heart. As a control, a mouse to which the same amount of saline solution was administered instead of the lactic acid bacteria was used.

Figure 16:
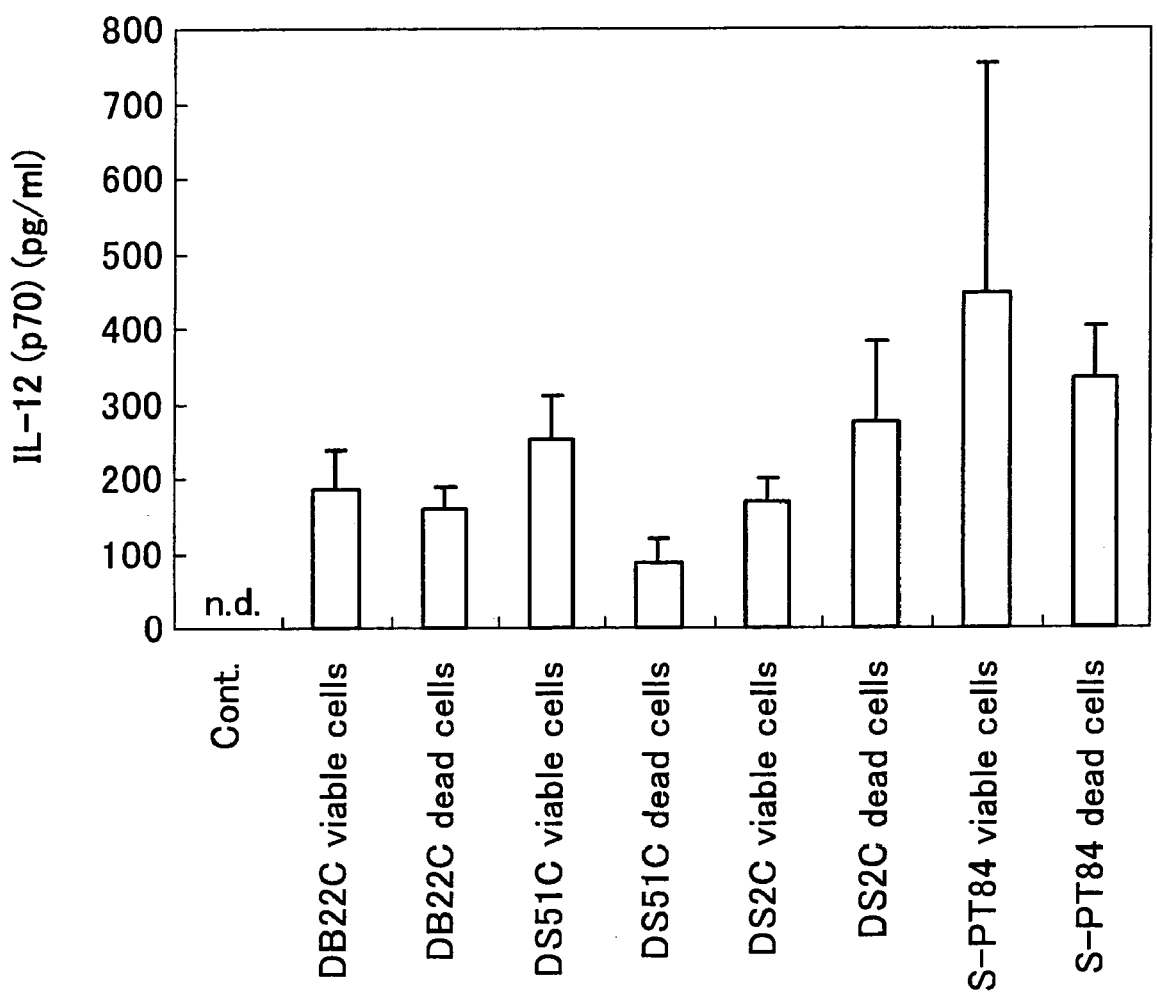
FIG. 16 is a graph representing the results of measurement on serum IL-12 concentration in response to intraperitoneal administration of 4 kinds of lactic acid bacteria (DB22C, DS51C, DS2C, and DS84C(S-PT84)) either as heat-killed cells or viable cells.

After the blood was collected, the serum was collected by centrifugation. The IL-12 concentration in the serum was measured with the OptEIA (BD Pharmingen). The results are shown in FIG. 16.

As in the case of FIG. 3, the amount of serum IL-12 was greatest for samples to which DS84C (S-PT84) was administered. As is also clear from FIG. 16, the amount of IL-12 was higher for the samples to which the viable cells of DS84C (S-PT84) were administered than for the samples to which the dead cells were administered.

Producing Example 1

Tablet

An S-PT84-containing medicament (tablet) was produced according to the following procedures.

A mixture containing 66.7 g of a dried pulverized powder of S-PT84, 232.0 g of lactose, and 1.3 g of magnesium stearate was punched with a single punch tableting machine, so as to produce tablets each having a diameter of 10 mm and a weight of 300 mg.

Producing Example 2

Yoghurt

S-PT84 fermented milk with a 21% solid milk component was added to commercially available milk, and the mixture was allowed to stand for 3 days so as to prepare yoghurt. The resulting yoghurt had a desirable flavor.

Producing Example 3

Lactic Acid Bacteria Drinks

By using S-PT84, a lactic acid bacteria beverage was prepared with the compositions shown in Table 4. The resulting lactic acid bacteria beverage had a desirable flavor.

TABLE 4

| Compositions | Parts by weight |
| --- | --- |
| S-PT84 fermented milk with 21% solid milk component | 14.76 |
| Fructose glucose syrup | 13.31 |
| Pectin | 0.5 |
| Citric acid | 0.08 |
| Flavoring agent | 0.15 |
| Water | 71.2 |
| Total | 100 |

The invention being thus described, it will be obvious that the same way may be varied in many ways. Such variations are not to be regarded as a departure from the spirit and scope of the invention, and all such modifications as would be obvious to one skilled in the art are intended to be included within the scope of the following claims.

INDUSTRIAL APPLICABILITY

A composition according to the present invention, if ingested as food or drink, or administered as medicaments, enables the immune function to be activated and thereby suppresses reduction of immune functions. Further, by adjusting the balance of immune function, adverse effects of excess immune function on the body can be suppressed.

A composition according to the present invention can be implemented as health food or medicaments with immuno-regulating activities. Therefore, the invention is useful is food industries and pharmaceutical industries.

The invention claimed is:

1. A composition comprising lactic acid bacteria which belong to *Lactobacillus pentosus*, and which have a weak assimilating activity or no assimilating activity for glycerol, and wherein the lactic acid bacteria are a *Lactobacillus pentosus* S-PT84 strain (Deposit Accession No. FERM BP-10028).

2. The composition as set forth in claim 1, wherein the lactic acid bacteria have immunoregulating activities and/or anti-allergy activities.

3. The composition as set forth in claim 2, wherein the lactic acid bacteria are an extracellular polysaccharide-producing strain.

4. The composition as set forth in claim 1, wherein the composition has immunoregulating activities.

5. The composition as set forth in claim 1, wherein the composition has anti-allergy activities.

6. The composition as set forth in claim 1, wherein the composition contains lactic acid bacteria as viable cells.

7. The composition as set forth in claim 4, wherein the composition is food, a drink, or a medicament.

* * * * *